(12) United States Patent
Miyata et al.

(10) Patent No.: US 6,881,194 B2
(45) Date of Patent: Apr. 19, 2005

(54) WIRE-STRANDED MEDICAL HOLLOW TUBE, AND A MEDICAL GUIDE WIRE

(75) Inventors: Naohiko Miyata, Nagoya (JP); Tomihisa Kato, Nagoya (JP); Kenji Miyata, Nagoya (JP); Toshiya Osawa, Nagoya (JP); Kazumi Matsuo, Nagoya (JP); Ryuji Kusuda, Nagoya (JP); Yoshinobu Nakagoshi, Nagoya (JP); Tadakazu Kato, Nagoya (JP)

(73) Assignee: Asahi Intec Co., Ltd., Nagoya (JP)

( * ) Notice: Subject to any disclaimer, the term of this patent is extended or adjusted under 35 U.S.C. 154(b) by 225 days.

(21) Appl. No.: 10/100,160

(22) Filed: Mar. 19, 2002

(65) Prior Publication Data

US 2002/0151823 A1 Oct. 17, 2002

(30) Foreign Application Priority Data

Mar. 21, 2001 (JP) ....................................... 2001-081416
Aug. 10, 2001 (JP) ....................................... 2001-243937

(51) Int. Cl.⁷ ........................... A61B 5/00; A61M 25/00
(52) U.S. Cl. ........................................ 600/585; 604/264
(58) Field of Search ............................... 600/433–435, 600/585; 604/93.01, 264, 523–529

(56) References Cited

U.S. PATENT DOCUMENTS

| | | | |
|---|---|---|---|
| 4,579,127 A | | 4/1986 | Haacke |
| 4,932,419 A | * | 6/1990 | de Toledo ................... 600/585 |
| 5,373,619 A | * | 12/1994 | Fleischhacker et al. ........ 29/451 |
| 5,376,083 A | * | 12/1994 | Mische ........................ 604/264 |
| 5,840,046 A | * | 11/1998 | Deem ........................... 600/585 |
| 5,984,877 A | * | 11/1999 | Fleischhacker, Jr. ........ 600/585 |
| 6,589,227 B1 | * | 7/2003 | Klint ........................... 604/524 |

FOREIGN PATENT DOCUMENTS

| | | |
|---|---|---|
| EP | 0 200 919 A1 | 11/1986 |
| EP | 0 826 389 A2 | 3/1998 |
| EP | 1 040 843 A1 | 10/2000 |
| JP | 11-025758 | 1/1999 |
| WO | WO 96/07351 | 3/1996 |

* cited by examiner

*Primary Examiner*—Charles Marmor
(74) *Attorney, Agent, or Firm*—Morgan Lewis & Bockius LLP

(57) ABSTRACT

In a wire-stranded hollow tube (1), a plurality of metallic wires (8) preformed with a predetermined forming rate are twisted along a circular line into a careless hollow configuration. When twisting the metallic wires (8), the neighboring metallic elements (1a, 1a) are subjected to compression with no gap between the neighboring metallic elements (1a, 1a). This increases a contact pressure between the neighboring metallic elements (1a, 1a) to attain a good tightness with a good circularity and diametrical uniformity secured therebetween, thus preventing the wire-stranded hollow tube (1) from inadvertently collapsing. A tightness is strengthened between the neighboring metallic elements (1a, 1a) when the metallic elements (1a, 1a) of different helical pitch are used. By applying the wire-stranded hollow tube (1) to a medical guide wire, a quick torque response and a good torque transmissibility are ensured which lead to a good manipulatability with a favorable follow-on capability.

10 Claims, 25 Drawing Sheets rotation

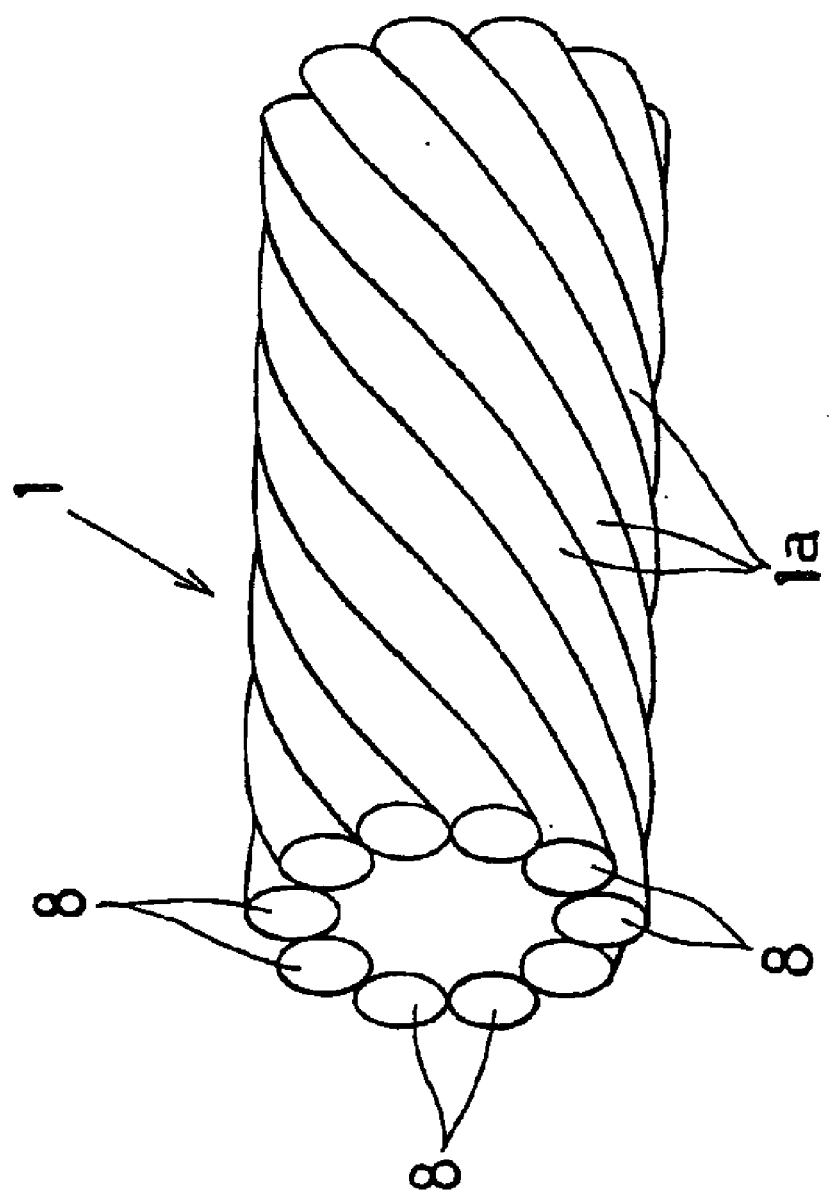

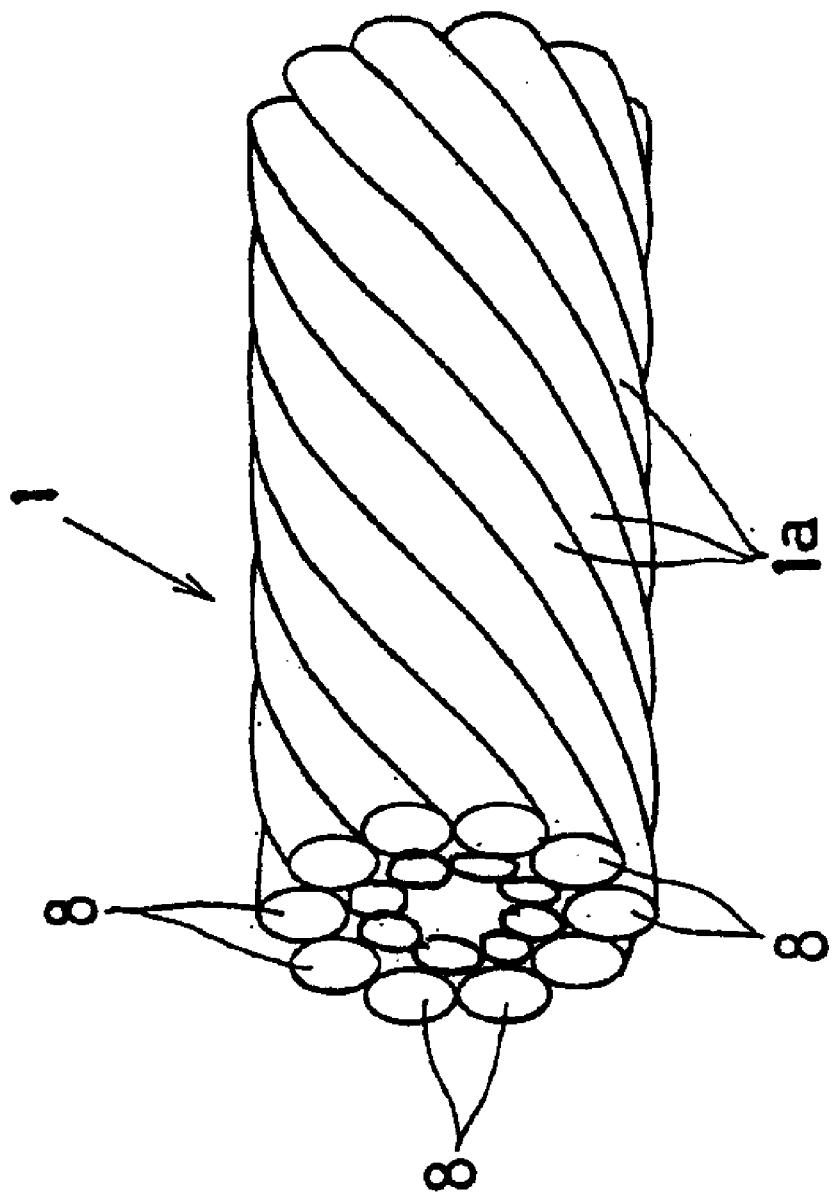

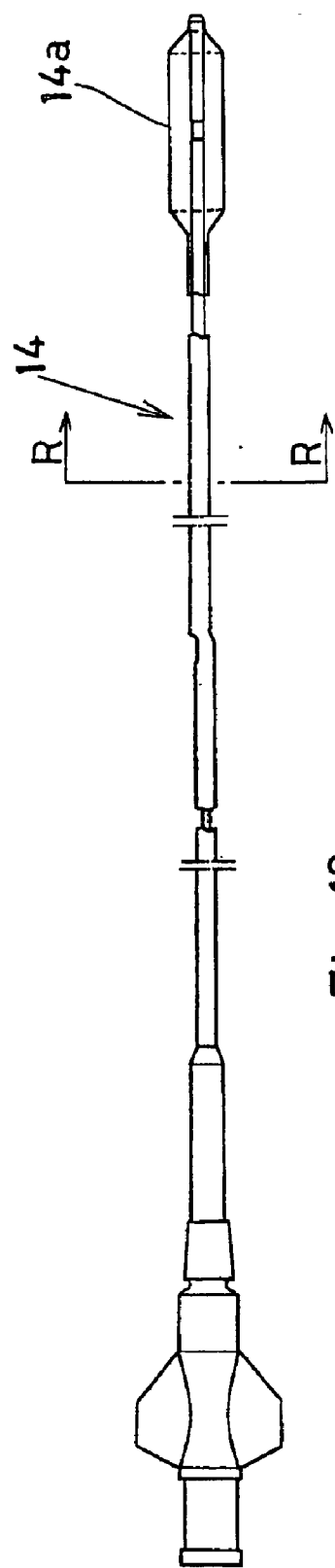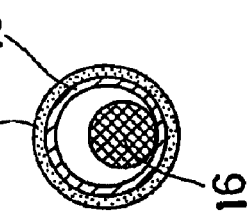

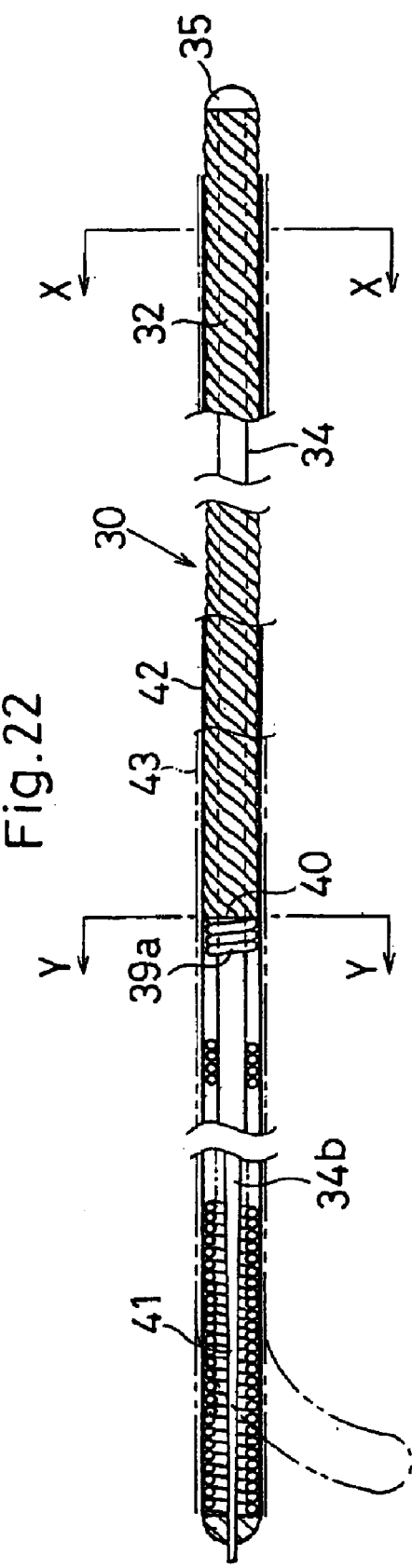
Fig. 22
Fig. 24
Fig. 23

La = AB

Lb = AC

La < Lb

WIRE-STRANDED MEDICAL HOLLOW TUBE, AND A MEDICAL GUIDE WIRE

BACKGROUND OF THE INVENTION

1. Field of the Invention

The invention relates to a wire-stranded medical hollow tube in which a plurality of metallic wires are twisted along a circular line to be shaped into a coreless hollow configuration, and particularly concerns to a medical tube body and a medical guide wire into which the wire-stranded medical hollow tube is incorporated.

2. Description of Prior Art

As a general medical tube body, a synthetic resin tube and a flexible tube (T) has been introduced in which a helical spring (S) is embedded in a synthetic resin (P) as shown in FIG. 34. The helical spring (S) is single wound or multiple wound by a spring forming machine. To take a five-turn wound helical spring (U) as an example in FIG. 35, a gap (G) is likely to appear at every five-turn wound end (N). The gap (G) develops remarkably in particular when an initial winding tension is not enough upon forming the helical spring (u).

This not only imparts the helical spring (U) with a convexso-concave outer appearance but result in a loss of torque under the presence of the gap (G) when transmitting the torque through the helical spring (U). An accumulated loss of the torque exceedingly reduces the torque transmissibility. On the other hand, the helical spring (U) increases its rigidity when the initial winding tension is strengthened too much upon forming the helical spring (U). Under the increased rigidity, the frictional resistance increases between the helical spring (U) and an inner wall of a wound and small blood vessel every time when advancing the helical spring (U) to pass through wound portions of the wound and small blood vessel. The increased frictional resistance deteriorates a manipulatability when the helical spring (U) is applied to a medical guide wire.

A Laid-open Japanese Patent Application No. 11-25758 (prior reference) discloses a wire-stranded hollow body in which wire elements are twisted along a circle line to overcome the drawbacks which a multiple coaxial cable wire usually has, so as to attain a lightweight structure with a smooth surface and a good circularity. The wire-stranded hollow body disclosed by the prior reference, however, is applied practically to an electric cable wire and has no substantial suggestion about an improved tightness between the wire elements to ensure a quick torque response and a good torque transmissibility.

Therefore, the present invention has been made with the above disadvantages in mind, it is a main object of the invention to provide a medical tube body and a medical guide wire which has a wire-stranded hollow tube formed by a plurality of metallic wires twisted along a circular line into a coreless hollow configuration with no gap appeared between the neighboring metallic wires by increasing a contact pressure therebetween to attain a good tightness between the neighboring metallic wires with a good circularity and a good diametrical uniformity to ensure a quick torque response and good torque transmissibility with the least play, thereby leading to a good manipulatability with a favorable follow-on capability.

SUMMARY OF THE INVENTION

According to the present invention, there is provided a wire-stranded hollow tube in which a plurality of metallic wires are twisted along a circular line to be a coreless hollow configuration with the metallic wires preformed by a predetermined forming rate. This provides a uniform contact pressure between the neighboring metallic wires with no gap appeared therebetween. The contact pressure between the neighboring metallic wires can be strengthened by increasing a helical pitch (e.g., 7–8 times the line diameter of the metallic wires) of the metallic wires.

With the increased contact pressure between the neighboring metallic wires, a good tightness between the neighboring metallic wires is ensured to tightly unite the metallic wires together with a good circularity and a good diametrical uniformity. Providing a postforming treatment with the wire-stranded hollow tube unites the metallic wires all the more tightly together to prevent the wire-stranded hollow tube from inadvertently collapsing. With the forming rate in the range of 90–98% when preforming the metallic wires, the good circularity and the good diametrical uniformity are strengthened.

According to other aspect of the invention, the metallic wires are formed from different materials. The circularity and the diametrical uniformity are all the more improved.

According to other aspect of the invention, the wire-stranded hollow tube is incorporated into a medical tube body and a medical guide wire. At the time of manipulating the medical tube body and medical guide wire, a good manipulatability can be ensured with a quick torque response and a good torque transmissibility achieved with the least play permitted.

By using the wire-stranded hollow tube, the good manipulatability can be ensured with the quick torque response and the good torque transmissibility secured with the least play at the time of manipulating the medical guide wire. A helical convexso-concave undulation appearing on an outer surface of the wire-stranded hollow tube enables a manipulator to a firm grip with no finger slip so as to readily introduce the medical guide wire to reach a target area.

According to other aspect of the invention, a single elastic elongation core is placed within a hollow portion of the wire-stranded hollow tube. This provides the medical guide wire with an improved pushability when inserting the medical guide wire deep into human body.

A synthetic resin layer is coated with an outer extension of the elongation core. The synthetic resin layer serves as a protection for the elongation core, and at the same time, providing the medical guide wire with a smoothness and a thrombus-repellent property. Adding an X-ray impervious agent (radiopaque agent) to the synthetic resin layer enables the manipulator to an X-ray photography. A hydrophilic resin film coated with the synthetic resin layer increases the smoothness and the thrombus-repellent property.

According to other aspect of the invention, a metallic helical spring is wound around a front end of the outer extension. The metallic helical spring contains a radiation-impervious agent. This enables the manipulator to confirm a leading end of the medical guide wire with a good flexibility maintained in the medical guide wire.

With the metallic helical spring wound around the outer extension by its entire axial length, the flexibility increases compared to the case in which the outer extension is coated with the synthetic resin layer. This flexibility makes it possible to flexibly follow the outer extension along a wound and small blood vessel, and whereby smoothly introducing the medical guide wire deep into the wound and small blood vessel.

According to other aspect of the invention, a synthetic resin layer is coated with an outer surface of the wire-stranded tube, and a hydrophilic resin film is provided on the synthetic resin layer. This provides the medical guide wire with an increased smoothness and thrombus-repellent property.

According to other aspect of the invention, the wire-stranded hollow tube is formed of different metallic wires. One is a Ni—Ti alloy wire and the other is a stainless steel wire (material stipulated by SUS) to cite an example. When these two different wires are subjected to diameter-reduction by means of a swaging or die drawing work, the hard Ni—Ti alloy wire tightly engages against the stainless steel wire to plastically deform the stainless steel wire. This increases a contact area between the Ni—Ti alloy wire and the stainless steel wire to more tightly unite these metallic wires together so as to strengthen the torque transmissibility, compared to the case in which the metallic wires are of the same material and of the identical hardness.

According to other aspect of the invention, the wire-stranded hollow tubes are concentrically arranged to form a multilayered configuration. The multilayered structure provides the medical guide wire with a flexibility, a durability and a stable manipulatability in the winding direction.

According to other aspect of the invention, a pressure sensor is incorporated into the medical guide wire to measure a blood pressure upon inserting the medical guide wire into the blood vessel. When the medical guide wire is inserted into the wound and small blood vessel, the wire-stranded hollow tube keeps its cross section substantially circular at the wound portions without deforming into a flat configuration. Keeping the circular cross section permits blood streams smoothly without disturbing them, thus enabling the manipulator to a precise blood pressure measurement and monitoring for an extended period of time with the least variation.

BRIEF DESCRIPTION OF THE DRAWINGS

A preferred form of the present invention is illustrated in the accompanying drawings in which:

FIG. 2 is a perspective view of a wire-stranded hollow tube according to a first embodiment of the invention;

FIG. 2a is a perspective view of an embodiment having a plurality of wire-stranded hollow tubes concentrically arranged;

FIG. 11 is a plan view of a balloon catheter;

FIG. 12 is an enlarged cross section taken along the line R—R of FIG. 11;

FIG. 22 is a perspective view of a medical guide wire in which the wire-stranded hollow tube is applied to the medical guide wire according to a fourth embodiment of the invention;

FIG. 23 is an enlarged longitudinal cross sectional view taken along the line Y—Y of FIG. 22;

FIG. 24 is an enlarged longitudinal cross sectional view taken along the line X—X of FIG. 22;

DETAILED DESCRIPTION OF THE PREFERRED EMBODIMENTS

According to a first embodiment of the invention, a wire-stranded hollow tube 1 (FIG. 2) is in a strand structure in which a plurality of metallic wires 8 are placed along a cicular line and twisted with the use of a rope twisting machine.

Figure 1:
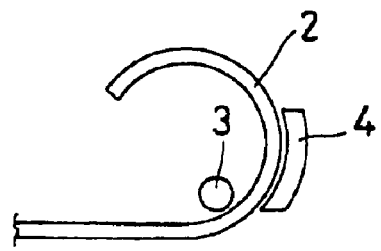
FIGS. 1, 1a, 1b and 1c are explanatory views comparatively showing how working transmutation layers are Induced when a coil forming machine and a rope stranding machine are used.
Figure 1A:
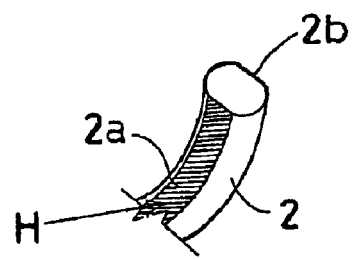

Upon deforming a metallic wire 2 with the use of a coil forming machine as shown in FIGS. 1 and 1a, an inner side of the metallic wire 2 tightly engages against an elevated pin 3, and an outer side of the metallic wire 2 tightly engages against a guide plate 4. This likely produces a work hardened layer (H) as a working transmutation layer on both sides 2a, 2b of the metallic wire 2.

Figure 1B:
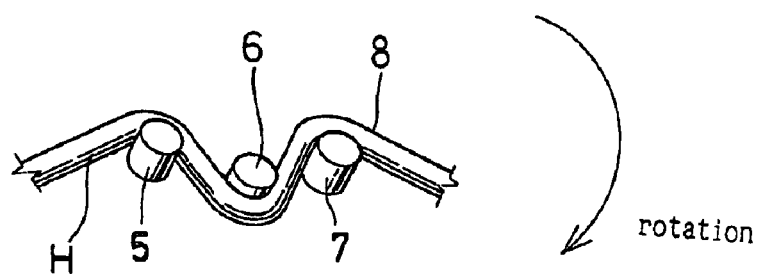
Figure 1C:
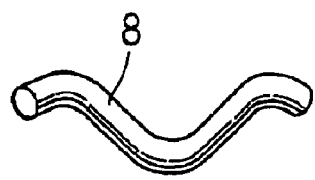
Figure 3:
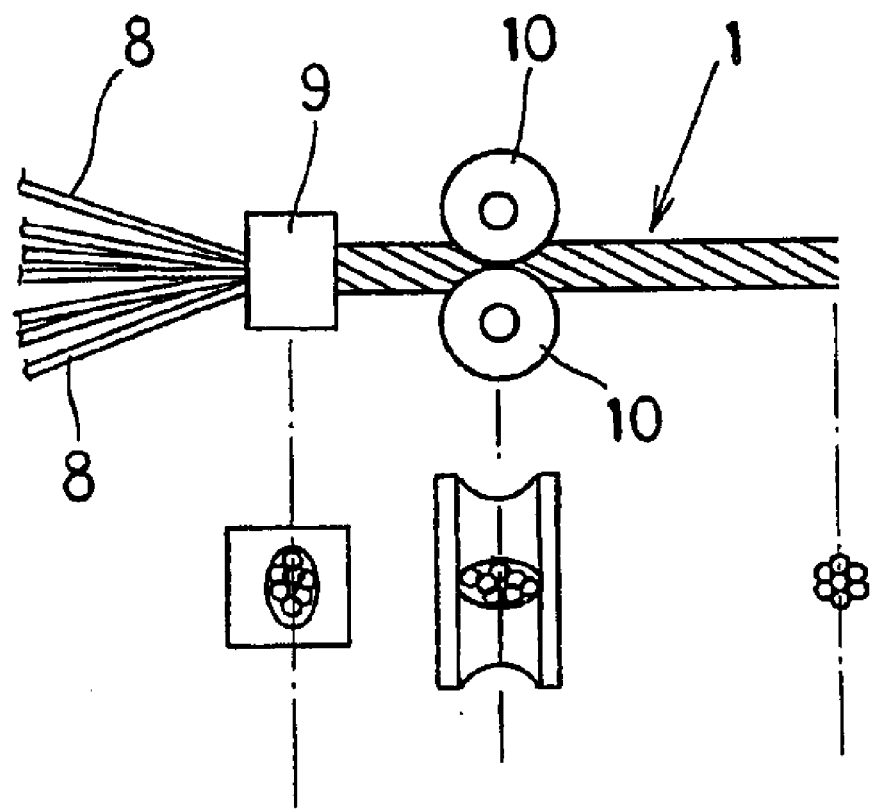
FIG. 3 is a schematic view showing how the wire-stranded hollow tube is formed.

Upon deforming a metallic wire 8 with the use of the rope twisting machine as shown in FIGS. 1b and 1e, the metallic wire 8 is twisted while being pulled upon weaving through three guide pins 5, 6 and 7 at the time when preforming the metallic wire 8. This provides the work hardened layer (H) on an entire surface of the metallic wire 8. Upon preforming the metallic wire 8, a forming rate falls in the range of 90–98% (preferably 90–95%). This provides the metallic wire 8 with an increased flexibility, an improved wear-resistance while removing a residual stress due to the metallic wire 8 being twisted. Releasing the residual stress prevents a spring-back and jumping-out phenomena when severing the metallic wire 8 at a predetermined length.

The metallic wires 8 are twisted along the circular line to form the wire-stranded hollow tube 1 with the use of the rope twisting machine. Neighboring line elements 1a, 1a of the metallic wires 8 engage tightly to each other without generating any gap therebetween because the neighboring line elements 1a, 1a are subjected to compression force when twisted. A helical pitch (corresponding to a screw lead) is determined to be 7–8 times larger than the line diameter of the metallic wire 8 (e.g., 0.43×(7–8)=3.01 –3.44 mm).

Upon postforming a rope structure which passes through a vice tool 9 as shown in FIG. 2, the rope structure is rolled between rollers 10, 10 to form the wire-stranded hollow tube 1 which ensures a good circularity and a good diametrical uniformity.

Namely, the rope structure thus stretched is severed at an appropriate length, and the core wires are withdrawn from the rope structure in which the metallic wires 8 were wound around the core wires. As the core wires, a bundle of soft line wires (e.g., mild steel) can be used so that the core wires are easily withdrawn. Alternatively, any line member can be used, an outer diameter of which is smaller than an inner diameter of the wire-stranded hollow tube 1.

The neighboring line elements 1a, 1a are tightly compressed to increase a contact pressure therebetween to unite the metallic wires 8 together, thus preventing the wire-stranded hollow tube 1 from inadvertently collapsing. With the neighboring line elements 1a, 1a tightly engaged each other, a good torque transmissibility can be achieved with a good wetting relationship secured between the neighboring line elements 1a, 1a.

It is to be noted that a tensile, compression or winding type preforming method may be used, otherwise a preforming method can also be used in which a difference of speed is converted to a tensile force.

From a view point of performance, the wire-stranded hollow tube 1 is compared to other counterpart pieces.

Figure 4:
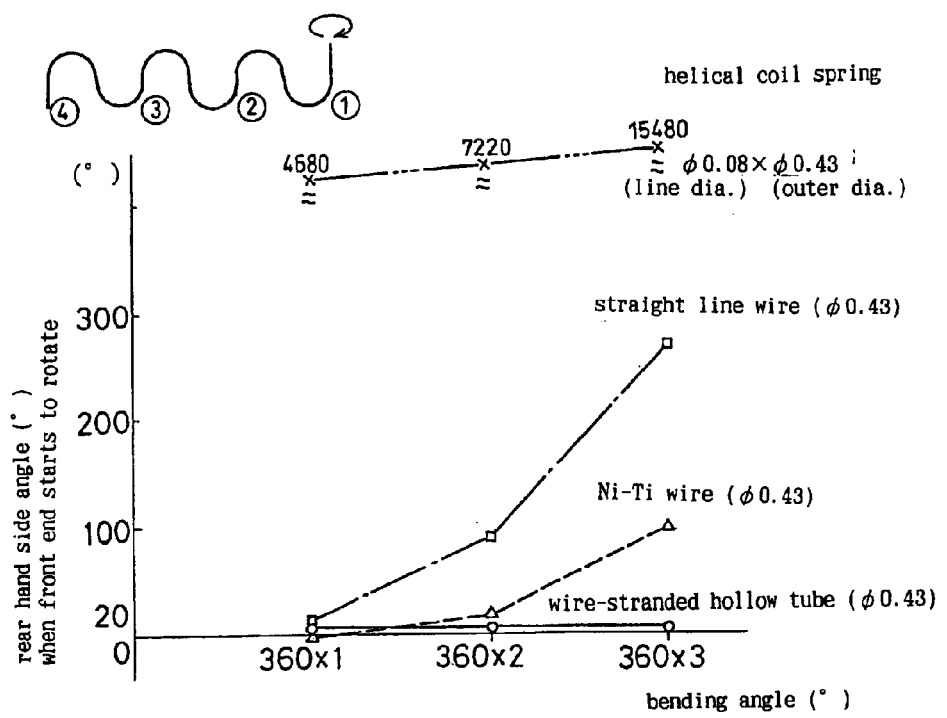
FIG. 4 is a graphical representation showing a rotational angle when each piece starts to rotate.

The following relationship (FIG. 4) is obtained concerning to an angle of a rear hand side in which each piece starts to rotate when inserted into a predetermined wound tube area.

Wire-stranded hollow tube (φ0.43)<Ni—Ti wire (φ0.43) <straight line wire (φ0.43)<<helical coil spring (φ0.43).

With the wire-stranded hollow tube 1 superior in torque response and torque transmissibility, a high torque sensitivity is ensured so that a front end swiftly rotates with a small amount of the torque given to the rear hand side.

In this instances, the wire-stranded hollow tube 1 has twelve line elements (φ0.085 mm) wound around a line core (φ0.265 mm). The line core is withdrawn to form the wire-stranded hollow tube 1 which measures φ0.43 mm in outer diameter.

The helical coil spring is in a single wound helical spring structure in which a line element (φ0.08 mm) is used to have φ0.43 mm in outer diameter.

The Ni—Ti wire is solid and shaped in a linear configuration to have 0.43 mm in outer diameter.

The straight line wire is of a solid stainless steel rectified to increase its linearity with the use of a bearing, roller or the like.

Figure 5:
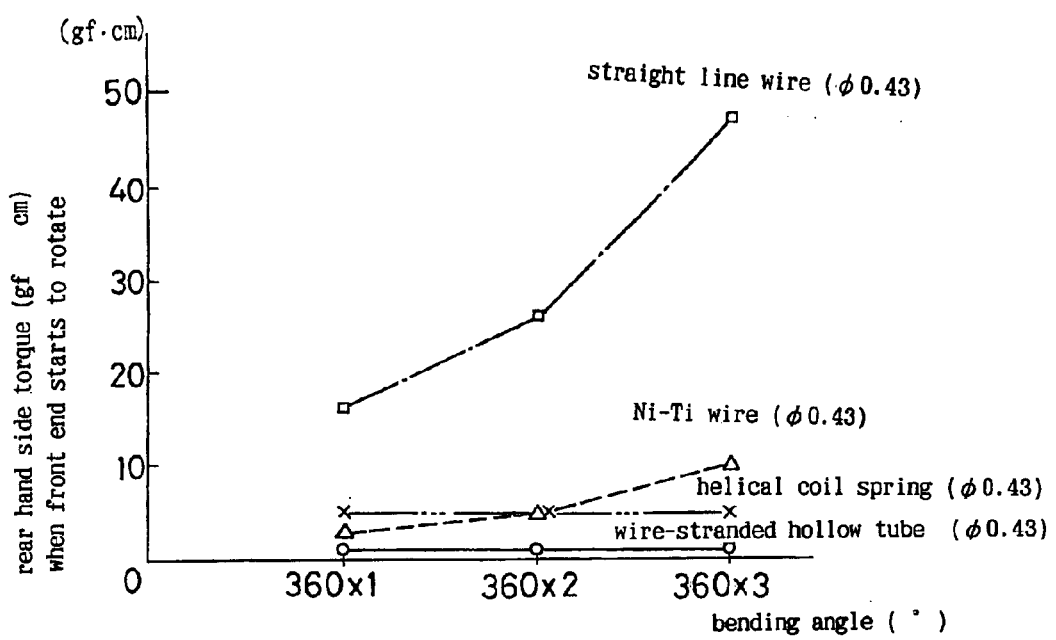
FIG. 5 is a graphical representation showing a rotational torque when each piece starts to rotate.

The following relationship (FIG. 5) is obtained concerning to a torsional torque of the rear hand side in which each piece starts to rotate when inserted into the predetermined wound tube area.

Wire-stranded hollow tube (φ0.43)<helical coil spring (φ0.43)<Ni—Ti wire (φ0.43)<straight line wire (φ0.43).

Due to the high torque sensitivity with the least play permitted between the neighboring elements 1a, 1a, the front end swiftly rotates with a small amount of the torque given to the rear hand side. Since the rear hand side takes many turns for the front end to start rotating in the helical coil spring, the helical coil spring is not well-suited to a practical use as understood from the graphical representation in FIG. 4.

Figure 6:
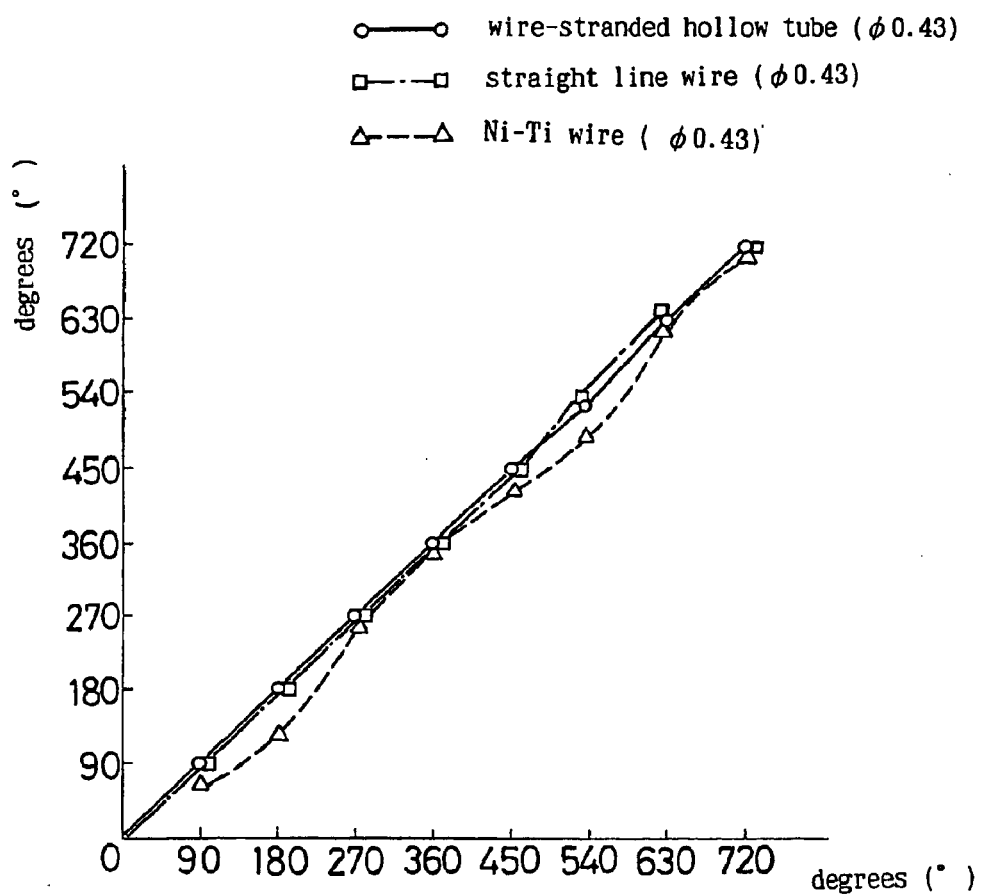
FIG. 6 is a graphical representation showing a linear characteristics when each piece starts to rotate in a normal direction.
Figure 7:
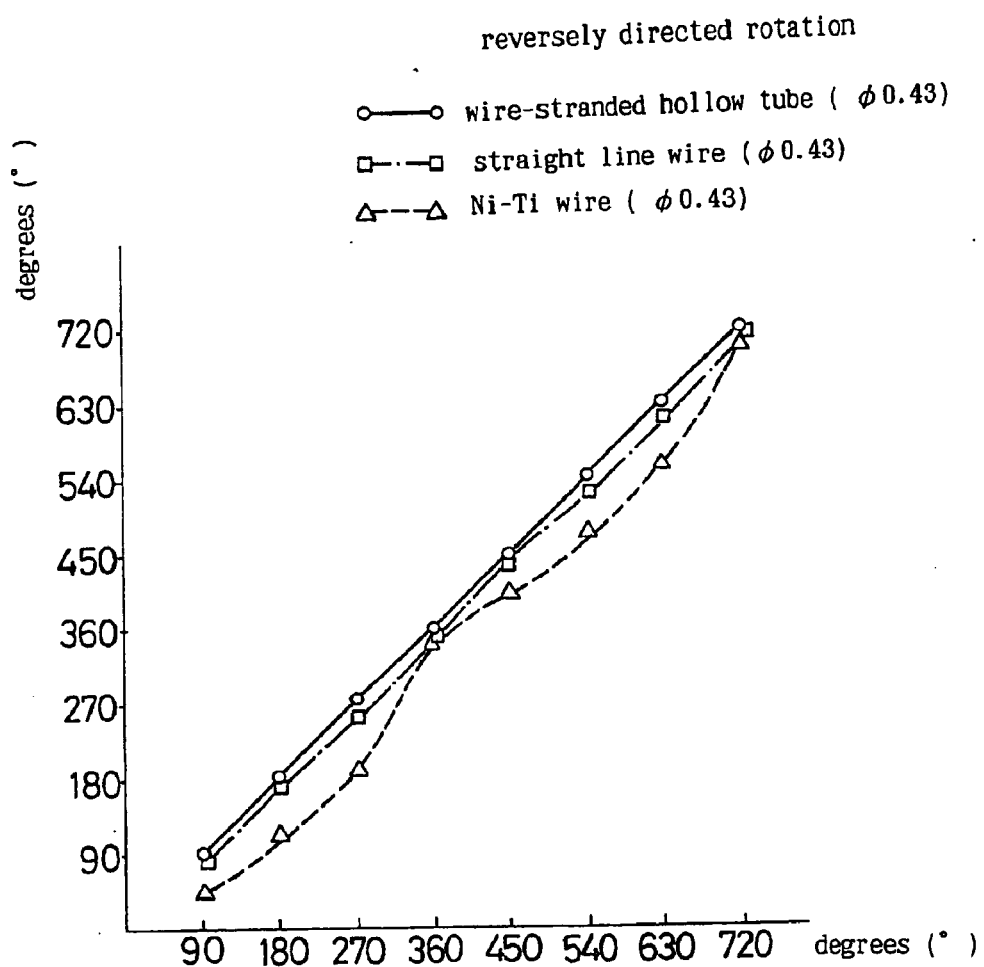
FIG. 7 is a graphical representation showing a linear characteristics when each piece starts to rotate in a reverse direction.

For the wire-stranded hollow tube 1, a good torque response (linear relationship) is ensured in normal and reverse directions in which no substantial delay is perceived in torque response between the rear hand side and the front end as shown in FIGS. 6 and 7.

For the solid line wire (straight line wire (φ0.43) and Ni—Ti wire (φ0.43)), a certain delay can be perceived in the follow-on capability. This tendency is remarkable for the Ni—Ti wire (φ0.43).

The difference of these characteristics depends on whether the counterpart piece has a hollow flexible structure or a solid rigidity structure. The wire-stranded hollow tube 1 is rendered into the hollow flexible structure so that the aforementioned torque response and torque transmissibility are surmised to be improved albeit the total bending angle increases with a decrease of torsion-resistant moment and rigidity.

Figure 8:
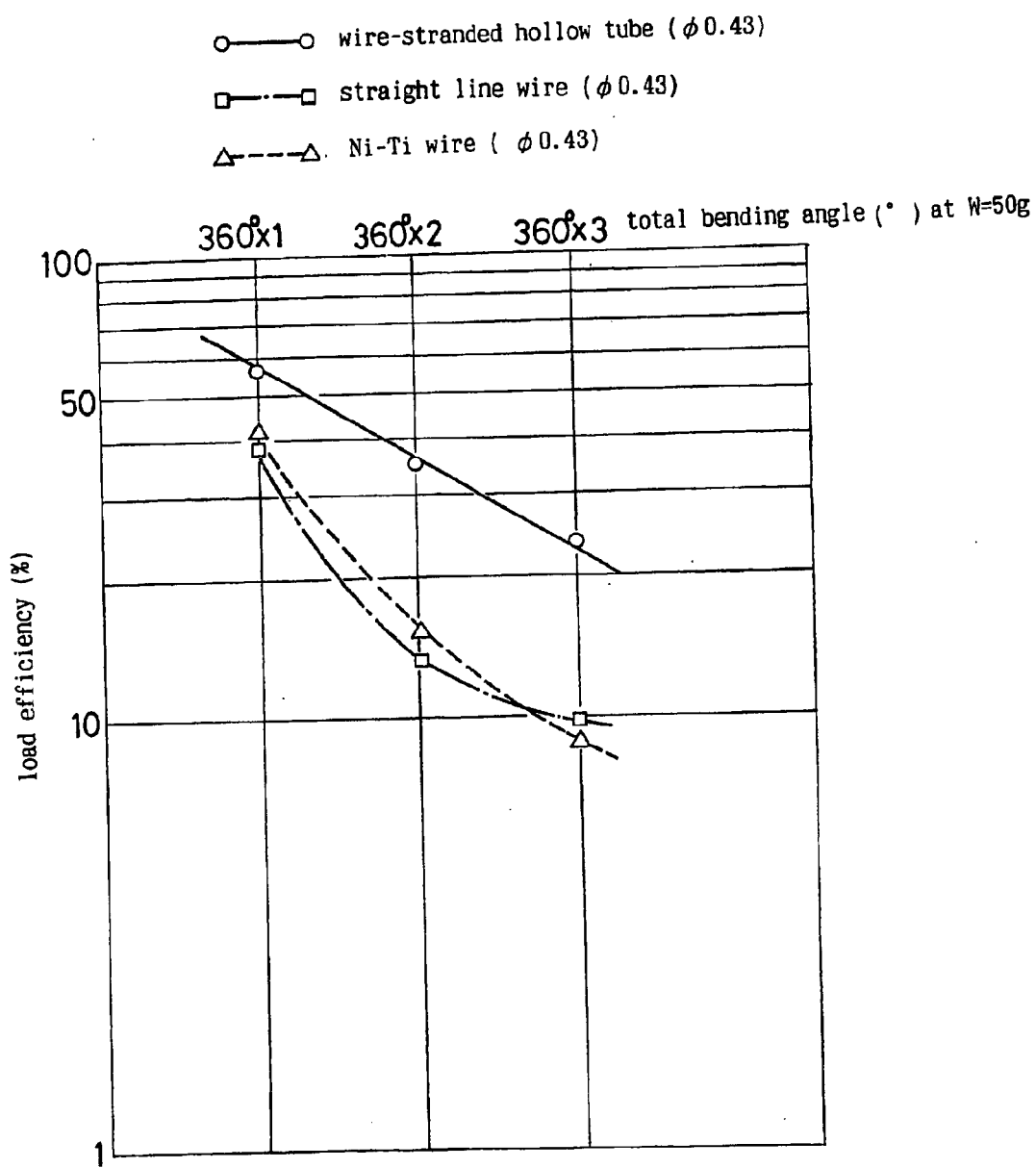
FIG. 8 is a graphical representation showing a load efficiency represented by a total bending angle when load is applied.

FIG. 8 shows a load efficiency (%) in terms of the total bending angle when a predetermined amount of load (e.g., approx. 0.049 N) is applied to each of the pieces. The graphical representation in FIG. 8 shows the following relationship in the load efficiency.

Wire-stranded hollow tube (φ0.43)>Ni—Ti wire (φ0.43) >straight line wire (φ0.43)

This indicates how lightweight the wire-stranded hollow tube is formed with the good manipulatability. The wire-stranded hollow tube 1 superior in torque response and torque transmissibility is well-suited to a medical tube body.

When the wire-stranded hollow tube 1 is applied to the medical tube body, the medical tube body exhibits a linear torque transmissibility with no significant torque variation. For this reason, the manipulator can advance the medical tube body precisely into a target area of the blood vessel.

Figure 34:
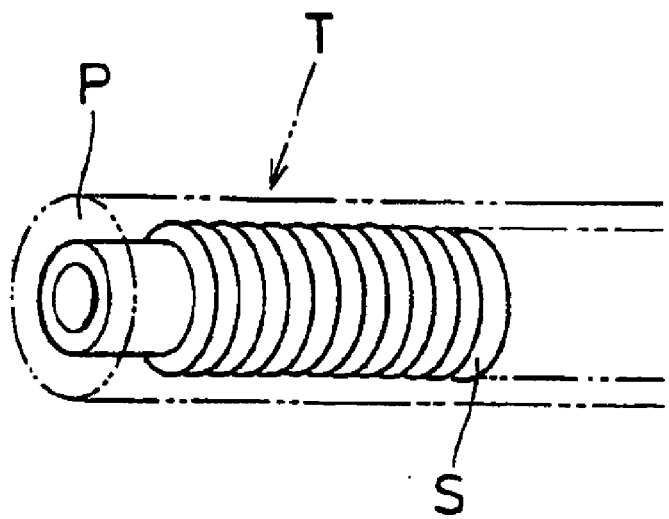
FIG. 34 is a perspective view of a prior medical tube body formed by a helical spring.
Figure 35:
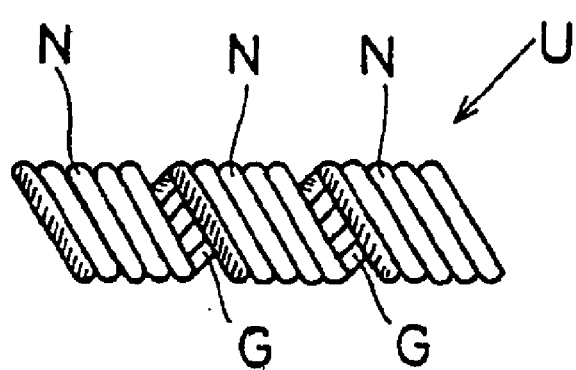
FIG. 35 is a plan view of the prior medical tube body formed by a helical spring.

As opposed to the prior art (FIGS. 34 and 35) in which the gap (G) is induced at the helical spring (S) to permit an irregular transmissibility and an uneven bending, the wire-stranded hollow tube 1 bends uniformly with a good linear torque transmissibility.

Figure 9:
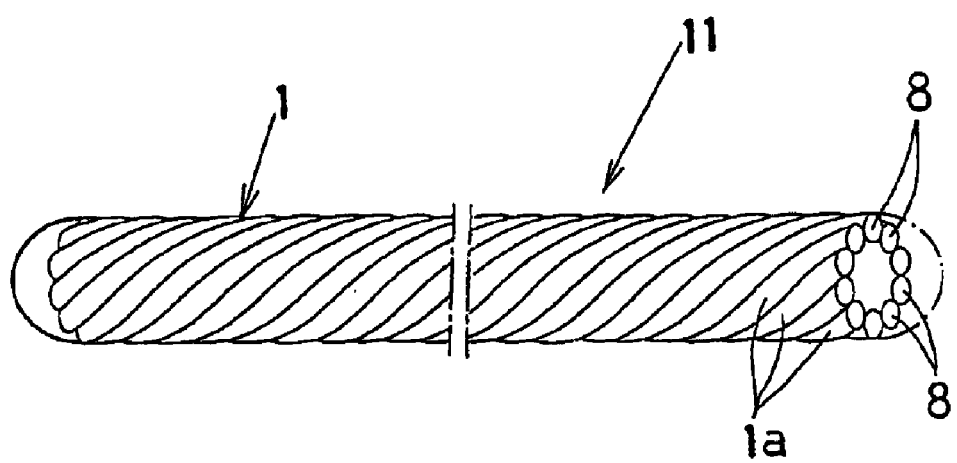
FIG. 9 is a perspective view of the medical guide wire.

FIG. 9 shows a medical guide wire 11 in which a core line (hoop line or the like) is inserted into the wire-stranded hollow tube 1 and both ends of the wire-stranded hollow tube 1 is soldered to the core line (not shown).

Then, an outer surface of the wire-stranded hollow tube 1 is coated with Teflon 4F (tetrafluoroethylene) to produce the medical guide wire 11 (usually referred to as "GW"). The same characteristics as the medical tube body has obtained in the previous embodiment are provided with the medical guide wire 11.

Figure 10:
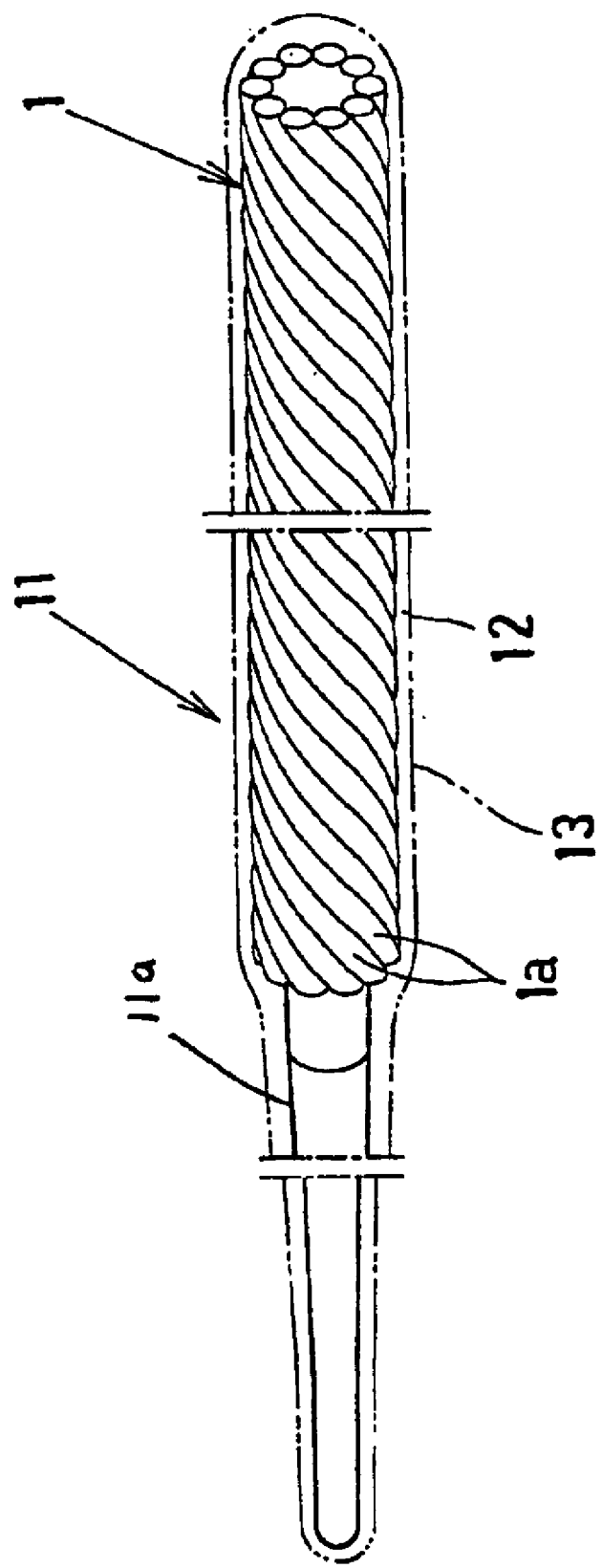
FIG. 10 is a perspective view of the medical guide wire when a thermoplastic synthetic resin layer and a hydrophilic resin film is coated with the medical guide wire.

FIG. 10 shows the medical guide wire 11 in which a small tube 11a is fixedly connected to the wire-stranded hollow tube 1. An outer surface of the medical guide wire 11 is coated with a thermoplastic synthetic resin 12 Teflon (tetrafluoroethylene) nylon, polyurethane or the like). On an outer surface of the thermoplastic synthetic resin 12, a hydrophilic polymer 13 (polyvinylpyrrolidone or the like) is coated.

The thermoplastic synthetic resin 12 may be coated with an inner surface of the medical guide wire 11 or may be coated with both the inner and outer surfaces of the medical guide wire 11. Instead of the thermoplastic synthetic resin 12, a metallic film may be formed by means of sputtering, evaporation or the like. Under the presence of the neighboring elements 1a, 1a twisted, the rear hand side of the medical guide wire 11 appears a convexso-concave undulation which prevents a finger slip to enable the manipulator to a firm grip.

FIGS. 11 and 12 show a balloon catheter 14 in which the wire-stranded hollow tube 1 is applied with an inflatable balloon 14a secured to the balloon catheter 14. The wire-stranded hollow tube 1 may be used instead of a hypotube 15. Alternatively, the wire-stranded hollow tube 1 may be used in lieu of a single unit wire 16 placed within the hypotube 15. To the single unit wire 16, a material stipulated in SUS or a Ni—Ti alloy (shape memory alloy) may be employed. The wire-stranded hollow tube 1 may be used to a medical endscope tube which generally has a structure identical to the medical tube body.

Figure 13:
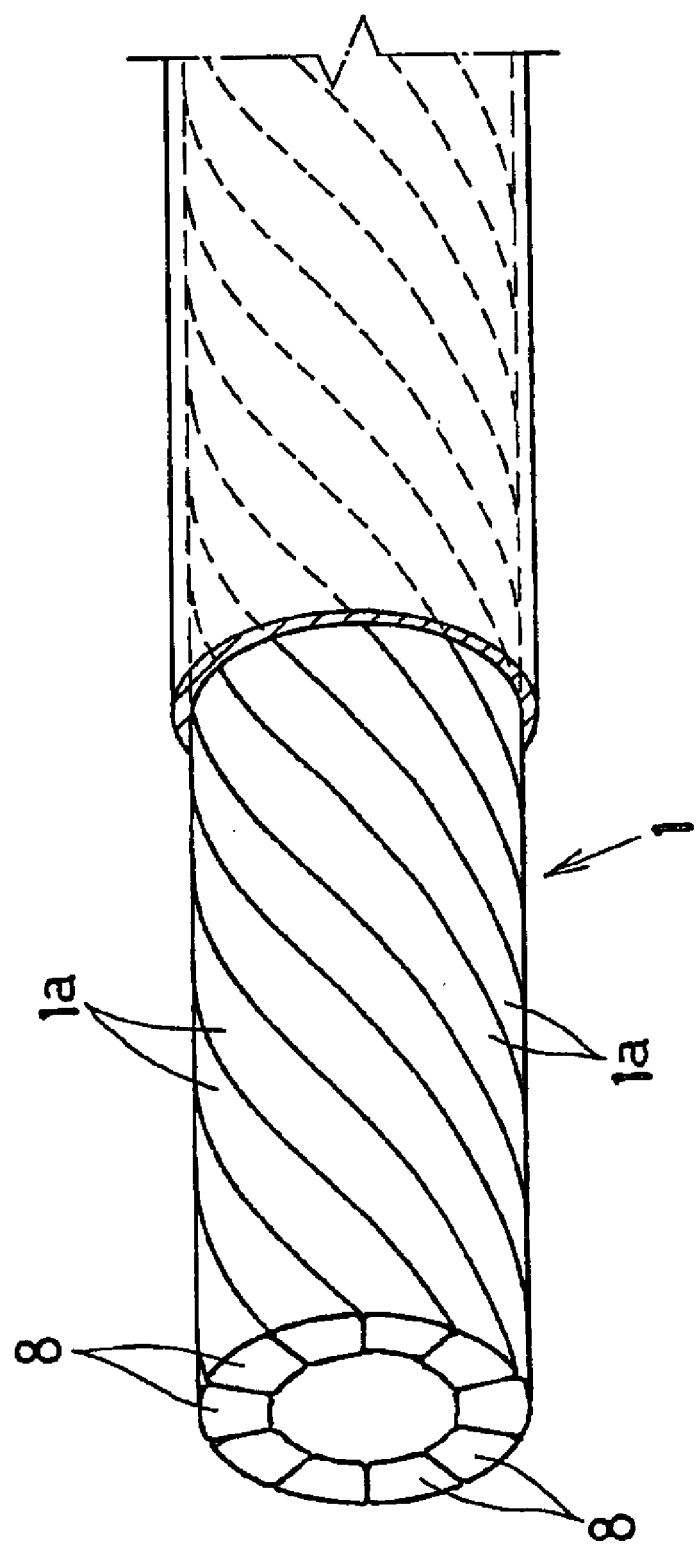
FIG. 13 is a perspective view of the wire-stranded hollow tube subjected to a die drawing work.

FIG. 13 shows the wire-stranded hollow tube 1 which is forced to reduce its diameter by means of a die drawing work. Due to the die drawing work, the neighboring elements 1a, 1a of the metallic wires 8 deform to tightly engage each other so as to produce a good cicularity with a uniform diameter substantially maintained. The die drawing work increases a contact pressure between the neighboring elements 1a, 1a to tightly unite the neighboring elements 1a, 1a to produce a quick torque response and a good torque transmissibility. When the wire-stranded hollow tube 1 is used to the balloon catheter, a good pushability is further ensured.

Figure 14:
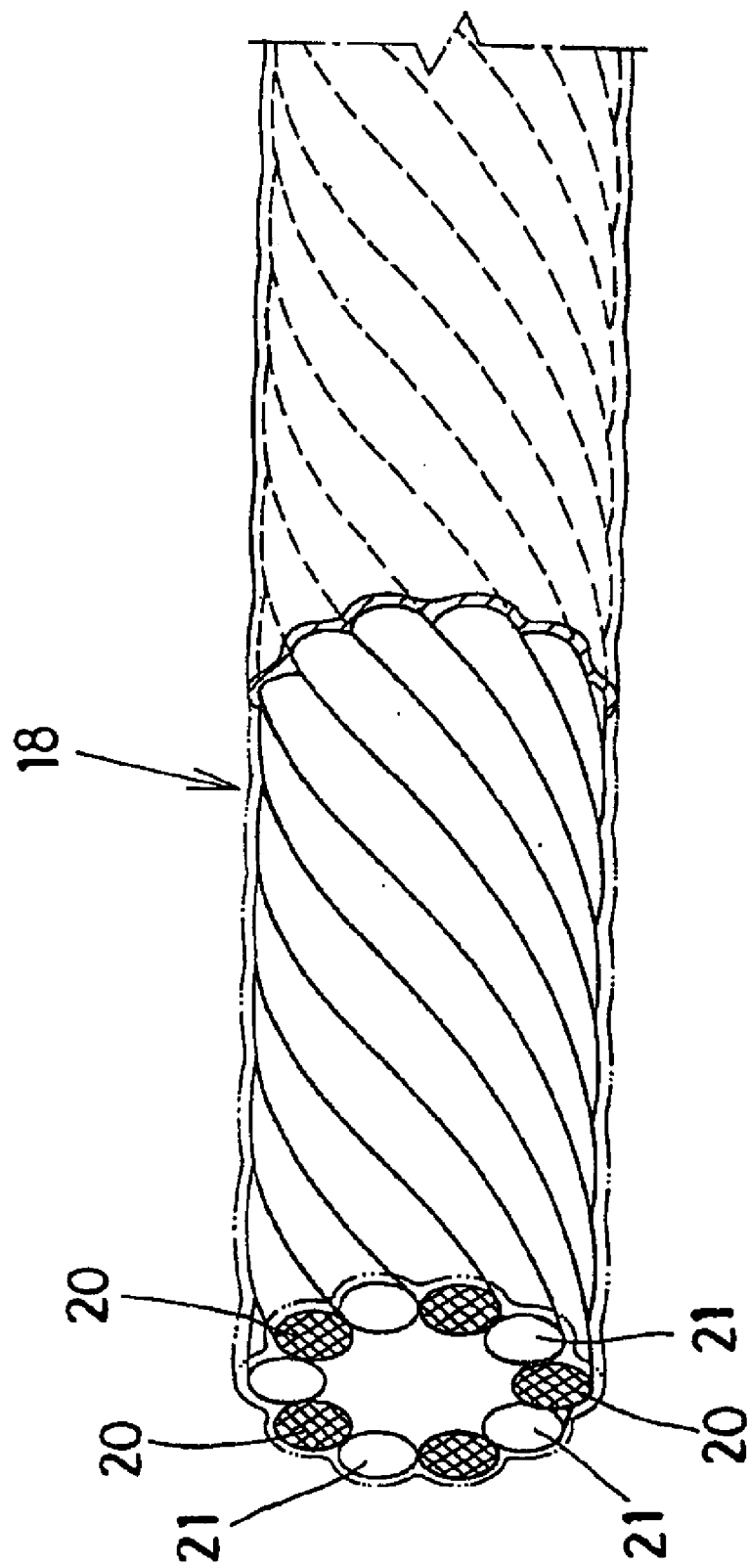
FIG. 14 is a perspective view of a modified wire-stranded hollow tube.

FIG. 14 shows a wire-stranded hollow tube 18 in which a stainless steel wire 20 and a Ni—Ti alloy wire 21 are stranded alternately to serve as different metallic wires.

Figure 15:
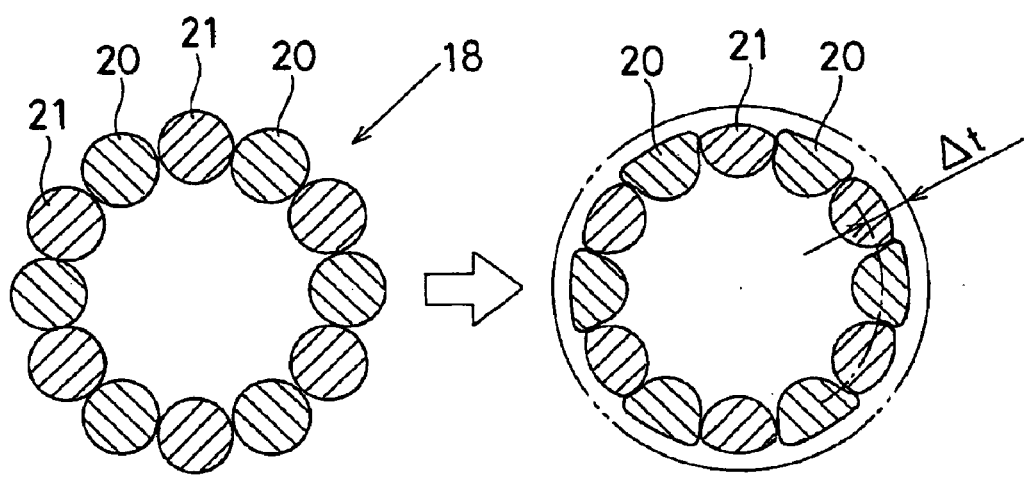
FIG. 15 is a schematic view comparatively showing the wire-stranded hollow tube subjected to a diameter reduction.

When the wire-stranded hollow tube 18 is forced to reduce its diametrical dimension by a compression shrinkage ($\Delta t$) with the use of the swaging or the die drawing work as shown in FIG. 15, the hard Ni—Ti alloy wire 21 tightly engages against the stainless steel wire 20 to deform the stainless steel wire 20. This makes the Ni—Ti alloy wire 21 contact with the stainless steel wire 20 with an increased contact area to tightly unite them together to achieve a more improved torque transmissibility.

Figure 16:
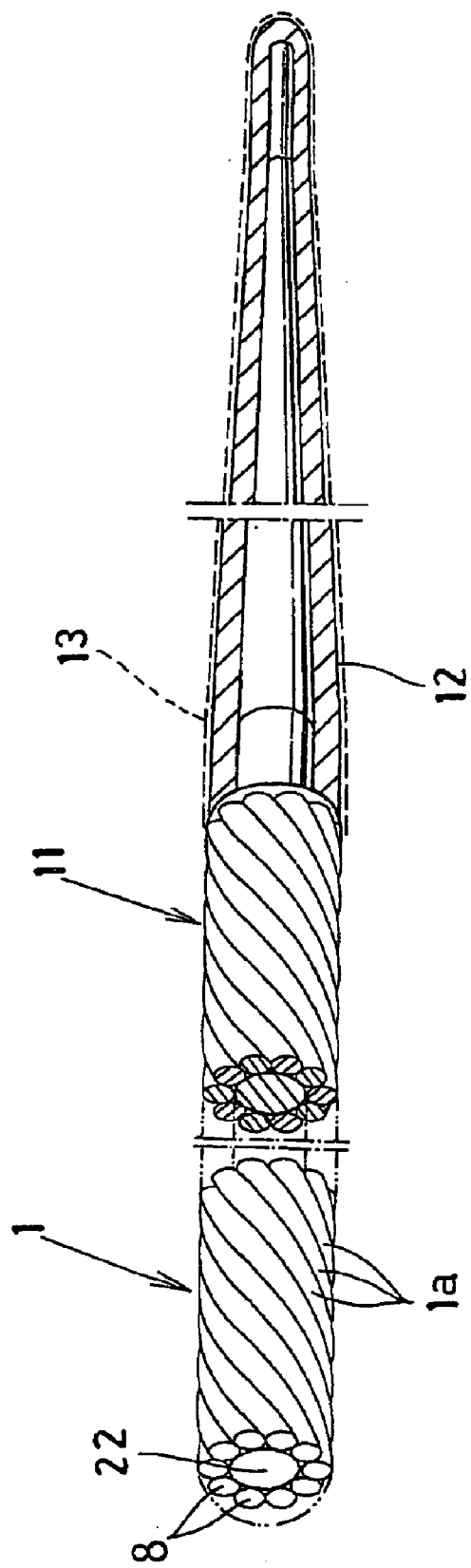
FIG. 16 is a perspective view of a medical guide wire in which the wire-stranded hollow tube is applied to the medical guide wire according to a second embodiment of the invention.
Figure 17:
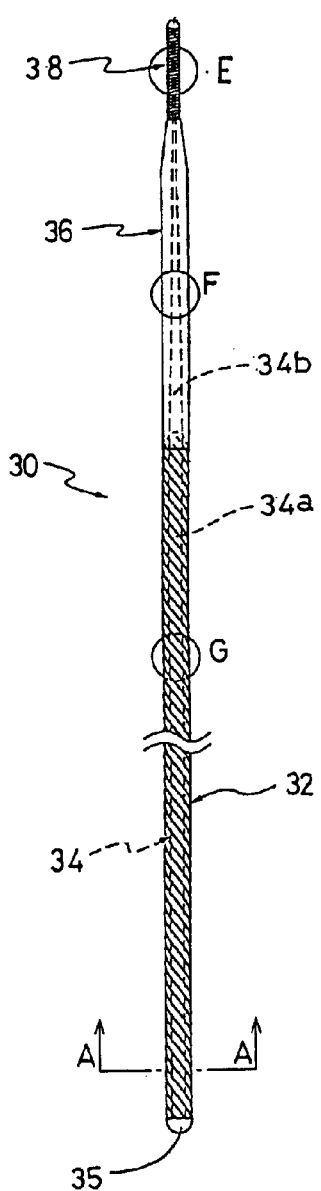
FIG. 17 is a perspective view of a medical guide wire in which the wire-stranded hollow tube is applied to the medical guide wire according to a third embodiment of the invention.
Figure 18:
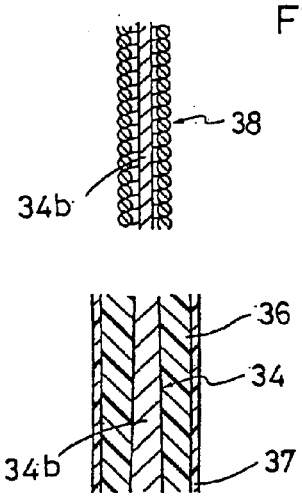
FIG. 18 is an enlarged longitudinal cross sectional view showing a circled portion E of FIG. 17.
Figure 19:
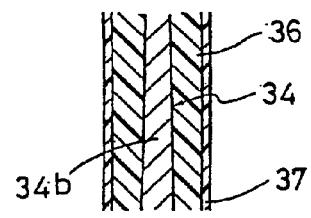
FIG. 19 is an enlarged longitudinal cross sectional view showing a circled portion F of FIG. 17.
Figure 20:
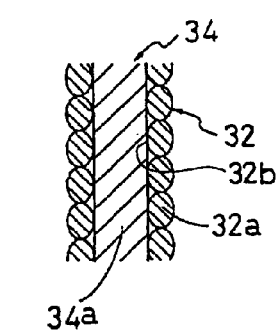
FIG. 20 is an enlarged longitudinal cross sectional view showing a circled portion G of FIG. 17.
Figure 21:
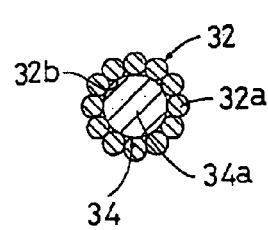
FIG. 21 is an enlarged latitudinal cross sectional view taken along the line A—A of FIG. 17.

FIG. 16 shows a second embodiment of the invention in which the wire-stranded hollow tube 1 is applied to the medical guide wire 11. To the wire-stranded hollow tube 1, an elongated core 22 is inserted, an outer diameter of which is slightly smaller than an inner diameter of the wire-stranded hollow tube 1. Both ends of the wire-stranded hollow tube 1 are soldered to the elongated core 22.

In this instance, the medical guide wire 11 is effective in particular when a pushability is needed in addition to a quick torque response. In this situation, the elongated core 22 may be in a solid or hollow configuration.

FIGS. 17–21 show a third embodiment of the invention in which a wire-stranded hollow tube 32 is applied to the medical guide wire 30. The medical guide wire 30 has the wire-stranded hollow tube 32 formed relatively longer by twisting many turns a plurality (e.g., 12) of metallic wires 32a, and having an elastic elongation core 34 which progressively decreases its diameterical dimension toward a front end of the elongation core 34. A synthetic resin tube 36 is fixed around the elongation core 34 except for a tapered-off portion of the elongation core 34. A front helical spring 38 is secured to surround the tapered-off portion of the elongation core 34.

As a basal side resin layer, an outer surface of the wire-stranded hollow tube 32 is coated with a fluoride-based resin layer (not shown) such as, for example, a polytetrafluoroethylene layer (PTFE), a thickness of which is approx. 8 $\mu$m. In order to provide a smoothness and a thrombus-repellant property, the basal side resin layer is formed by a hydrophobic synthetic resin such as a silicone resin in addition to the fluoride-based resin layer.

In the elongation core 34 located in a hollow portion 32b of the wire-stranded hollow tube 32, a basal end of the wire-stranded hollow tube 32 is plasma welded to a basal main body 34a together with a rear tip 35. A front end of the wire-stranded hollow tube 32 is soldered to the elongation core 34. As a material of the elongation core 34, used are a stainless steel, a piano wire and superelastic metals such as Ni—Ti alloy, Cu—Zn—Q alloy (Q=Al, Fe or the like), Ni—Ti—Q alloy (Q=Cu, Fe, V, Co or the like).

The synthetic resin tube 36 provides a flexibility with an outer extension 34b of the elongation core 34, and at the same time, protecting an area in which the synthetic resin tube 36 covers. By way of illustration, the synthetic resin tube 36 is formed by polyurethane, polyvinylchloride, polyester or the like. To the synthetic resin tube 36, a required amount of powder prescribed from barium sulfate, bismuth, tungsten or the like is added as an X-ray impervious agent. Coated with an outer surface of the synthetic resin tube 36 is a hydrophobic resin film 37 formed by polyvinylpyrrolidone (PVP), polyethylene glycol or the like in order to further provide the smoothness and the thrombus-repellent property.

A front helical spring 38 is secured to surround a leading end of the outer extension 34b, and fixed to the outer extension 34b by means of a soldering or an adhesive. The front helical spring 38 at least partly contains the X-ray impervious agent such as silver, platinum, bismuth, tungsten, Pt—Ni alloy or the like.

FIGS. 22–24 show a fourth embodiment of the invention. The fourth embodiment of the invention differs from the third embodiment of the invention in that instead of the synthetic resin tube 36 and the front helical spring 38, a continuous helical spring 39a formed with a stainless steel is secured to surround the outer extension 34b of the elongation core 34.

In this instance, a metallic wire ($\phi$0.17 mm in dia.) which is formed by the material stipulated in SUS 304 is used to the wire-stranded hollow tube 32. A metallic wire ($\phi$0.40 mm in dia.) which is formed by the material stipulated in SUS 304 is used to the elongation core 34. An equi-diametrical portion ($\phi$0.10 mm in dia.) resides at a front extension area (5.0 mm) of the elongation core 34. A metallic wire ($\phi$0.15 mm in dia.) which is formed by the material stipulated in SUS 304 is used to the continuous helical spring 39a which measures 0.89 mm in outer diameter.

The wire-stranded hollow tube 32 is soldered to the continuous helical spring 39a together with the elongation core 34 at their common junction 40. The continuous helical spring 39a is also bonded to the outer extension 34b of the elongation core 34 at a designated middle portion 41. Coated with outer surfaces of the wire-stranded hollow tube 32 and the continuous helical spring 39a are a synthetic resin layer (PTFE) 42, a thickness of which measures approx. 8 μm. On an outer surface of the synthetic resin layer 42, a hydrophobic resin film 43 is formed.

With the continuous helical spring 39a connected in series with the wire-stranded hollow tube 32, a good flexibility is provided with the medical guide wire 30, thus enabling the manipulator to effectively advance deep into the wound and small blood vessel by staunchly following on the wound and small configuration at the time of inserting the medical guide wire 30 into the serpentine blood vessel.

Figure 25:
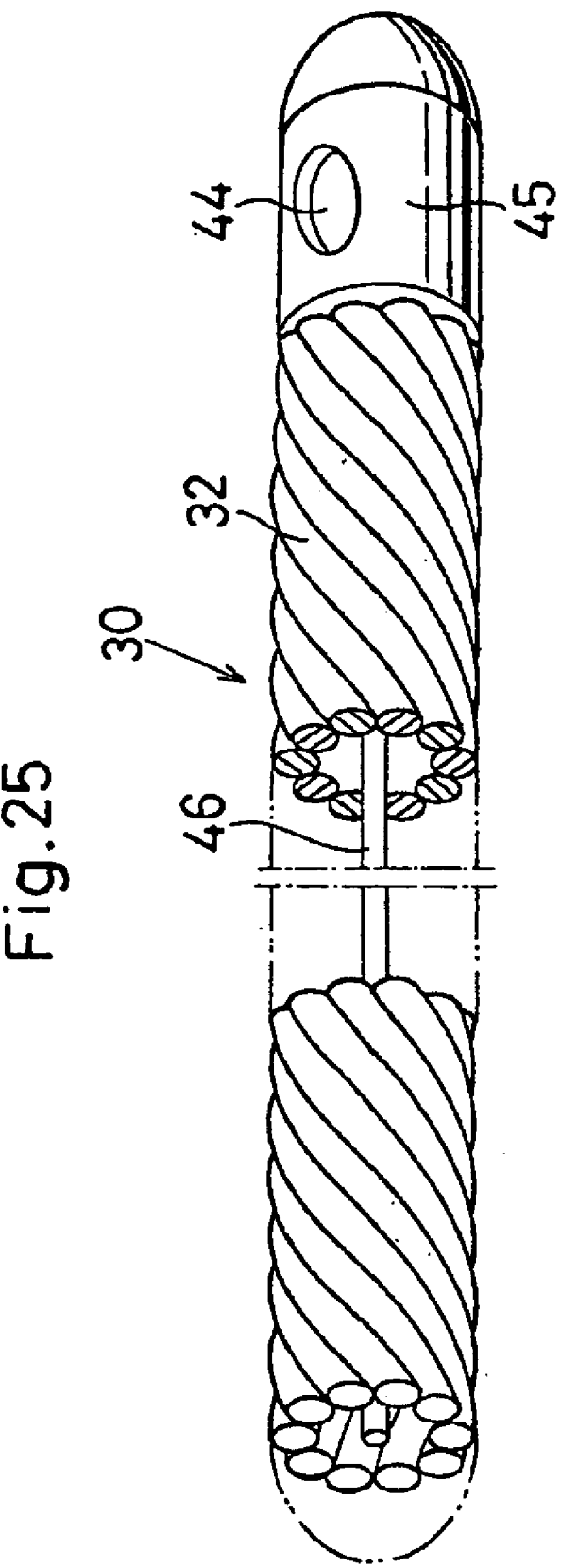
FIG. 25 is a perspective view of a medical guide wire according to a fifth embodiment of the invention.

FIG. 25 shows a fifth embodiment of the invention. In the fifth embodiment of the invention, a semiconductor type pressure sensor 44 is provided to measure a blood pressure value at front and rear portions of a stricture area of the blood vessel by inserting the medical guide wire 30 to reopen an obstructive coronary artery at the time of conducting a percutaneous transluminal coronary angioplasty (PTCA). Instead of the rear tip 35 of FIG. 22, the pressure sensor 44 is placed within a metallic tube 45 which is bonded to the wire-stranded hollow tube 32 by means of a soldering or the like. A microcable 46 (microwire connection) is stretched along an inner space of the medical guide wire 30.

Figure 26:
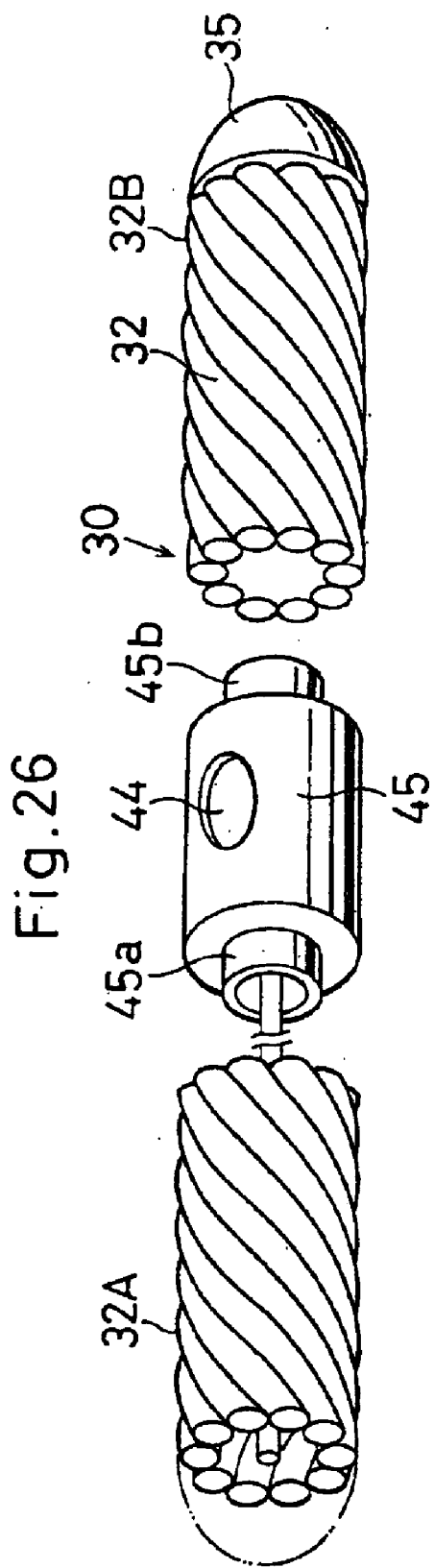
FIG. 26 is a perspective view of a medical guide wire according to a sixth embodiment of the invention.

FIG. 26 shows a sixth embodiment of the invention. In the sixth embodiment of the invention, the pressure sensor 44 is installed into the metallic tube 45, The wire-stranded hollow tube 32 is divided into a front majority piece 32A and a rear minor piece 32B, and the metallic tube 45 is provided between the front majority piece 32A and the rear minor piece 32B. Front and rear ends of the metallic tube 45 form the respective diameter-reduced tube connectors 45a, 45b. The diameter-reduced tube connectors 45a, 45b are connected and soldered to the front majority piece 32A and the rear minor piece 32B.

Figure 27:
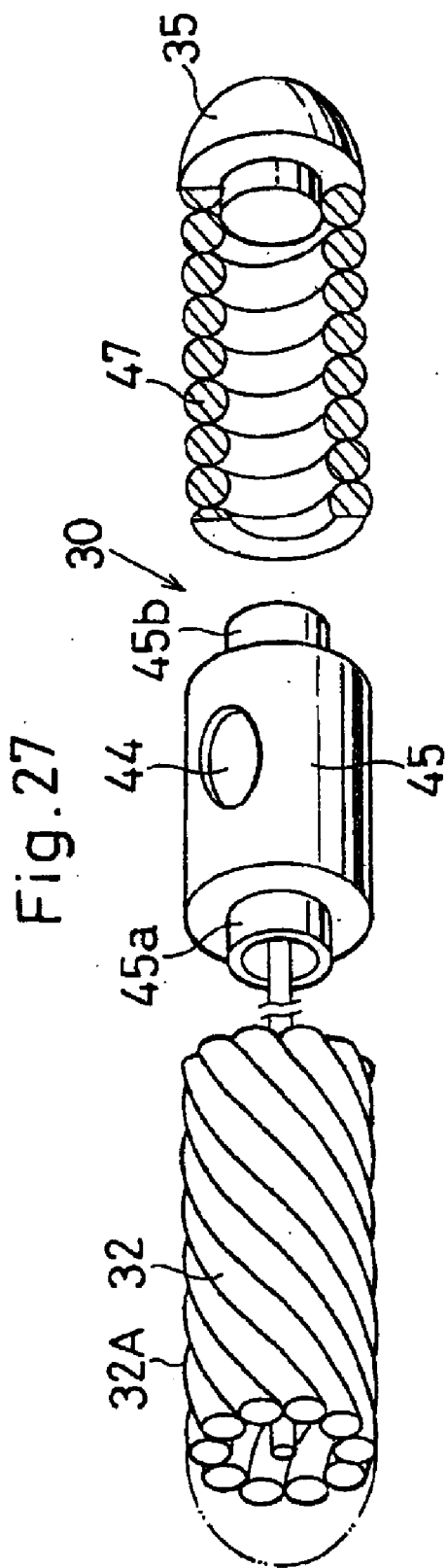
FIG. 27 is a perspective view of a medical guide wire according to a seventh embodiment of the invention.

FIG. 27 shows a seventh embodiment of the invention. In the seventh embodiment of the invention, a short helical spring 47 which contains the radiation-impervious agent (radiopaque agent) is provided instead of the rear minor piece 32B of FIG. 26.

In the fifth through seventh embodiments, the pressure sensor 44 is provided with the medical guide wire 30 to measure the blood pressure from the following reasons.

Figure 28:
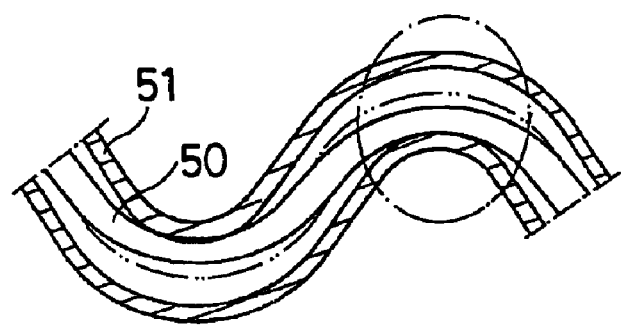
FIG. 28 is a schematic view showing how a general medical tube works when inserted into a wound and small blood vessel.

As a conventional medical guide wire, a medical tube 50 has been used in which a metallic wire net is covered with a synthetic resin coat, otherwise a synthetic resin is formed into tubular configuration. Upon inserting the medical tube 50 into a wound and small blood vessel 51 as shown in, FIG. 28, the medical tube 50 is subjected to deformation due to torsion, distorsion and bending when inserting the medical tube 50 into a wound portion of the blood vessel 51. When the medical tube 50 is subjected to the deformation, a precise blood pressure measurement and monitoring are rendered unable during the manipulating the medical tube 50 for an extended period of time.

Figure 29:
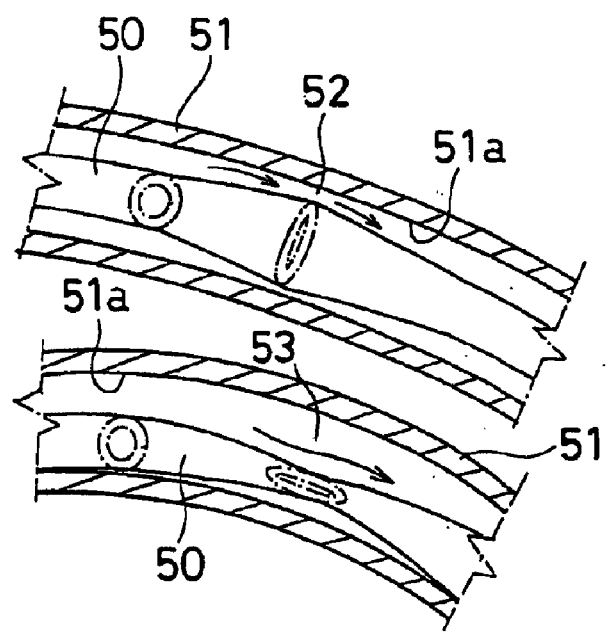
FIG. 29 is a schematic view showing how the general tube disturbs blood streams.

This is because the medical tube 50 is supposed to deform substantially flat to be elliptic in cross section as shown in FIG. 29. When the medical tube 50 deforms flat, blood paths 52, 53 vary its cross section between the medical tube 50 and an inner wall 51a of the blood vessel 51. The narrower blood path 52 allows blood streams to flow quicky, and the wider blood path 53 allows blood streams to flow slowly. Due to the difference of the blood stream velocity between the blood paths 52, 53, the blood stream is disturbed to fluctuate the blood pressure value measured by the pressure sensor. This tendency becomes more remarkable as the blood vessel becomes smaller. The situation renders the medical tube 50 unable to cope with the blood pressure measurement for the obstructive coronary artery.

On the contrary, the medical guide wire 30 according to the fifth through seventh embodiments enables the manipulator to use it smoothly in the wound and small coronary artery (1–3 mm), and thus ensuring a precise blood pressure measurement and monitoring during manipulating the medical guide wire 30 for an extended period of time.

Figure 30:
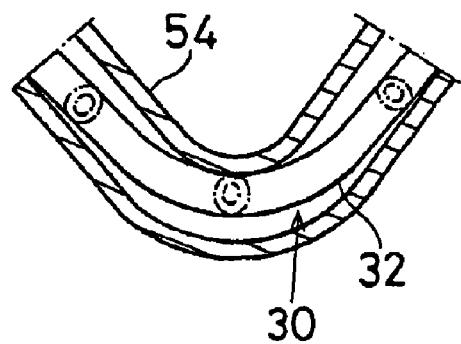
FIG. 30 is a schematic view of the medical guide wire which is advanced into the wound and small blood vessel.

This is surmisably because the medical guide wire 30 generally maintains a circular shape stable in cross section (FIG. 32) without deforming flat at a wound portion of a wound and small blood vessel 54 when inserting the medical guide wire 30 into the wound and small blood vessel 54 as shown in FIG. 30. Namely, the metallic wires 32a are each twisted to form the wire-stranded hollow tube 32 so that each metallic wire 32a relatively slides slightly along its helical line when the wire-stranded hollow tube 32 is bent. This keeps a tight engagement between the metallic wires 32a to generally maintain the circular shape stable in cross section as opposed to a single wound helical spring 55 which produces a gap (Sp) between the line elements 55a as mentioned hereinafter in detail.

Figure 31:
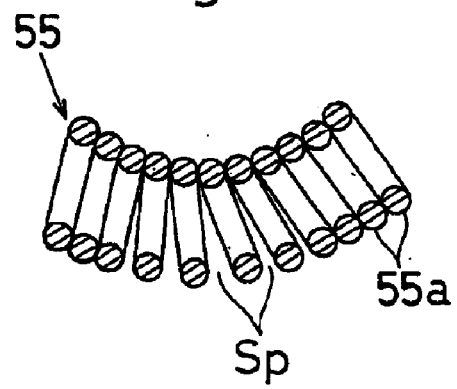
FIG. 31 is a schematic view of a single wound helical spring bent along the wound and small blood vessel.

The single wound helical spring 55 produces the gap (Sp) between the line elements 55a at the wound portion when the single wound helical spring 55 is bent as shown in FIG. 31, although the single wound helical spring 55 substantially maintains a circular shape in cross section without deforming flat at the wound portion. The gap (Sp) appeared between the line elements 55a causes a turbulence in the blood streams to fluctuate the blood pressure value measured by the pressure sensor.

Figure 32:
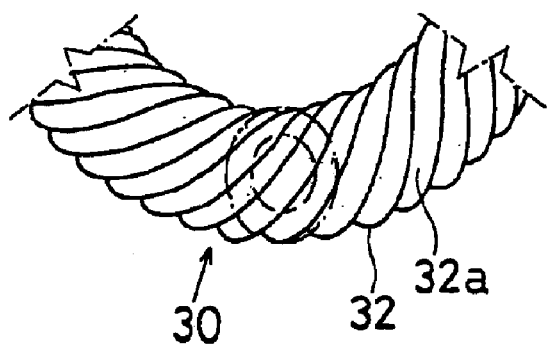
FIG. 32 is a schematic view of the wire-stranded hollow tube bent along the wound and small blood vessel.

In the medical guide wire 30, the wire-stranded hollow tube 32 only allows the metallic wires 32a to slightly slide along the helical line while maintaining the tight engagement between the metallic wires 32a to generally keep the circular shape stable in cross section without producing the gap between the metallic wires 32a as shown in FIG. 32. This resultantly generates no significant difference in the blood path between the medical guide wire 30 and the inner wall of the blood vessel to induce no significant turbulance in the blood streams, and thereby enabling the manipulator to the precise blood pressure measurement and monitoring for an extended period of time.

Due to helical grooves appeared between the metallic wires 32a, the blood streams are smoothly guided along the helical grooves to induce no significant fluctuation in the blood pressure value measured by the pressure sensor 44.

Figure 33:
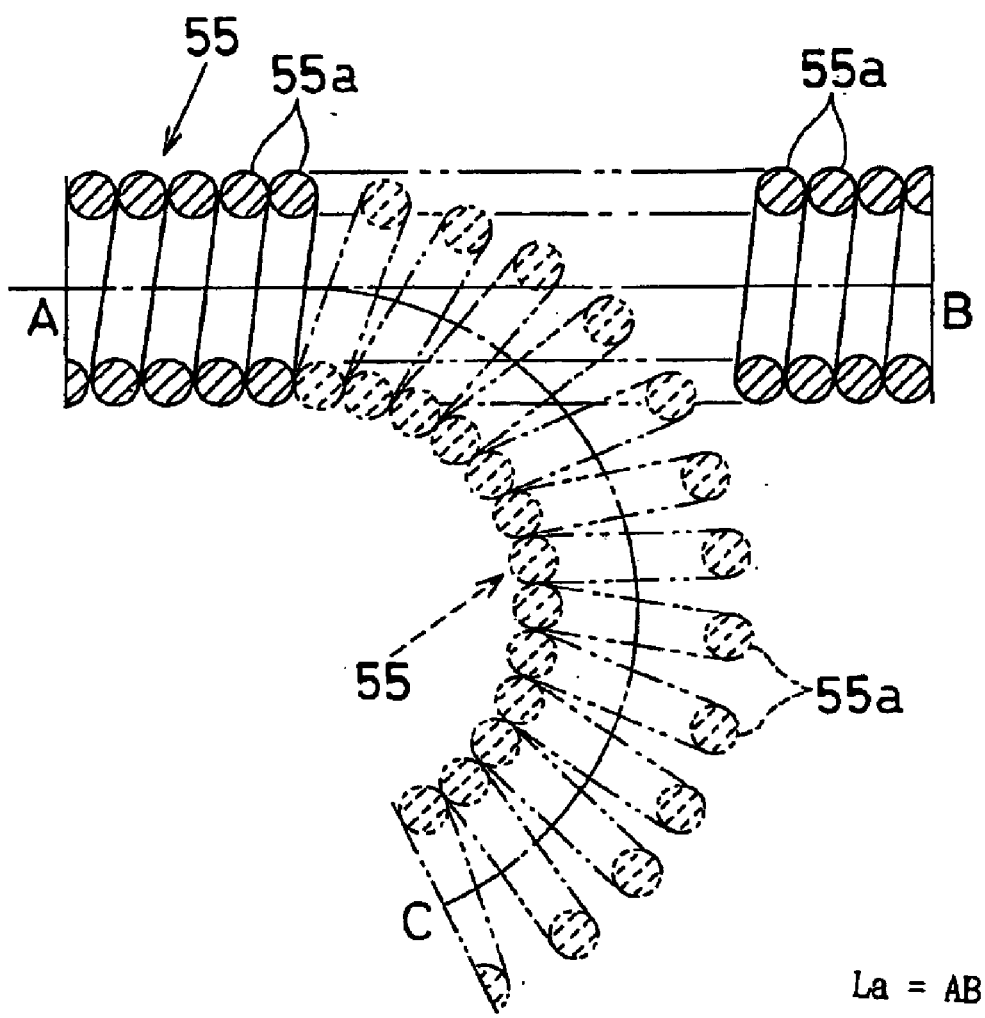
FIG. 33 is a schematic view showing how an axial length of the single wound helical spring is stretched.

When the single wound helical spring 55 is bent as shown in FIG. 33, the single wound helical spring 55 is expanded at its outer tensile side. This stretches the single wound helical spring 55 to make its axial length (Lb) longer than the original length (La). The axial length (La) stretches more remarkable as the single wound helical spring 55 is bent deeper. For this reason, the microcable of the pressure sensor 44 is feared to be snapped off due to a sufficient tensile force subjected to the microcable especially when advancing the single wound helical spring 55 deeply into the wound and small blood vessel 54.

In the medical guide wire 30 into which the wire-stranded hollow tube 32 is incorporated, the metallic wires 32a slightly slide each other to maintain the tight engagement therebetween without being expanded at the outer tensile side when the wire-stranded hollow tube 32 is deeply bent. This remains the axial length of the wire-stranded hollow tube 32 substantially unchanged. There is no fear that the microwire connection 46 is snapped off because no sufficient tensile force is subjected to the microcable 46 when advancing the medical guide wire 30 deeply into the wound and small blood vessel. The medical guide wire 30 is resultantly well-suited particularly when used to advance into an acutely wound portion of the wound and small blood vessel.

It is to be noted that outer surfaces of the wire-stranded hollow tube 32 and the short helical spring 47 are each coated with the synthetic resin layer over which the hydrophilic resin film is coated, although not shown.

MODIFICATION FORMS (a) The medical tube body and the medical guide wire may has a plurality (e.g., 2–3) of wire-stranded hollow tubes concentrically arranged to form a multilayered configuration.
(b) In the wire-stranded hollow tube, the metallic wire may be not only circular but also rectangular, triangular, pentagonal, hexagonal, polygonal and elliptic in cross section.
(c) The metallic wires of different helical pitch may be used to produce a tighter engagement between the neighboring metallic elements by providing the wire-stranded hollow tube with a strengthened compression.
(d) In general, the medical guide wire is 0.35–1.0 mm in outer diameter and the medical tube body is 0.4–3.0 mm in outer diameter, however these outer diameters are not confined merely to these statistics.

While there has been described what is at present thought to be preferred embodiments of the invention, it will be understood that modifications may be made therein and it is intended to cover in the appended claims all such modifications which fall within the scope of the invention.

What is claimed is:

1. A wire-stranded medical hollow tube comprising:

a plurality of metallic wires being twisted while being pulled upon weaving through guide pins to provide a work hardened layer on an entire surface of said metallic wires as a working transmutation layer, and stranded along a circular line to be formed into a coreless hollow configuration.

2. The wire-stranded medical hollow tube according to claim 1, wherein a forming rate which preforms said metallic wires is within a range of 90%–98%.

3. The wire-stranded medical hollow tube according to claim 1, wherein said plurality of metallic wires are made from different materials.

4. A medical guidewire formed by the wire-stranded medical hollow tube according to any one of claims 1–3.

5. The wire-stranded medical hollow tube according to claim 1, further comprising:

a single elastic elongation core inserted into a hollow portion of said wire-stranded hollow tube, and having a basal main body located within said wire-stranded hollow tube, and further having an outer extension which is diametrically smaller than said basal main body and extends beyond a front end of said wire-stranded hollow tube by a predetermined length; and a metallic helical spring wound around said outer extension of said elongation core by an entire axial length of said elongation core.

6. The wire-stranded medical hollow tube according to claim 5, wherein said metallic helical spring at least partially contains a radiation-impervious agent.

7. The wire-stranded medical hollow tube according to claim 1, an outer surface of which is subjected to a diameter-reduction procedure by one of a swaging and a die drawing work.

8. The wire-stranded medical hollow tube according to claim 1, wherein a plurality of said wire-stranded hollow tubes are concentrically arranged to form a multilayered configuration.

9. The wire-stranded medical hollow tube according to claim 1, wherein a pressure sensor is provided to measure a blood pressure when inserted into a human blood vessel.

10. A medical guide wire comprising:

a wire-stranded hollow tube formed by a plurality of metallic wires twisted along a circular line to be shaped into a coreless hollow configuration;

a single elastic elongation core inserted into a hollow portion of said wire-stranded hollow tube, and having a basal main body located within said wire-stranded hollow tube, and further having an outer extension which is diametrically smaller than said basal main body and extends beyond a front end of said wire-stranded hollow tube by a predetermined length; and a synthetic resin layer coated on an outer surface of said outer extension of said elongation core by a predetermined axial length of said elongation core.

* * * * *